United States Patent

Malon et al.

(10) Patent No.: US 8,582,860 B2
(45) Date of Patent: Nov. 12, 2013

(54) SIGNET RING CELL DETECTOR AND RELATED METHODS

(75) Inventors: Christopher Malon, Plainsboro, NJ (US); Matthew L. Miller, Princeton, NJ (US); Eric Cosatto, Red Bank, NJ (US)

(73) Assignee: NEC Laboratories America, Inc., Princeton, NJ (US)

( * ) Notice: Subject to any disclaimer, the term of this patent is extended or adjusted under 35 U.S.C. 154(b) by 802 days.

(21) Appl. No.: 12/496,795

(22) Filed: Jul. 2, 2009

(65) Prior Publication Data

US 2010/0172568 A1 Jul. 8, 2010

Related U.S. Application Data

(60) Provisional application No. 61/077,969, filed on Jul. 3, 2008.

(51) Int. Cl.
*G06K 9/62* (2006.01)

(52) U.S. Cl.
USPC .......................................................... 382/133

(58) Field of Classification Search
USPC ..................................... 382/133, 224; 706/20
See application file for complete search history.

(56) References Cited

U.S. PATENT DOCUMENTS

| 2006/0083418 A1* | 4/2006 | Watson et al. ................ 382/133 |
| 2006/0204053 A1* | 9/2006 | Mori et al. .................... 382/118 |
| 2010/0183217 A1* | 7/2010 | Seung et al. .................. 382/156 |
| 2011/0216953 A1* | 9/2011 | Callahan et al. .............. 382/128 |

FOREIGN PATENT DOCUMENTS

| JP | 2005-502872 A | 1/2005 |
| JP | 2008-009914 A | 1/2008 |
| JP | 2008-059319 A | 3/2008 |
| JP | 2008-112190 A | 5/2008 |

OTHER PUBLICATIONS

Tsunetake Kanatani and Yoshiaki Shirai, "Extraction of Corneal Endothelial Cells Using Energy Minimization," IEICE (The Institute of Electronics, Information and Communication Engineers) Transaction (Japanese Edition), vol. J80-D-II, No. 7, pp. 1705-1711 (Jul. 1997).

* cited by examiner

*Primary Examiner* — Neal Sereboff
*Assistant Examiner* — Maroun Kanaan
(74) *Attorney, Agent, or Firm* — Joseph Kolodka

(57) ABSTRACT

A detector and method for automatically detecting signet ring cells in an image of a biopsy tissue sample, includes finding in the image, points about which cell membranes appear in radial symmetry; selecting as candidate points, at least ones of the points that have an adjacent nuclei with a predetermined shape feature; and applying a convolutional neural network to the candidate points to determine which of the candidate points are signet ring cells.

12 Claims, 7 Drawing Sheets

SIGNET RING CELL DETECTOR AND RELATED METHODS

RELATED APPLICATIONS

This application claims the benefit of U.S. Provisional Application No. 61/077,969, filed Jul. 3, 2008, the entire disclosure of which is incorporated herein by reference.

This application is related to U.S. patent application Ser. No. 12/496,785 filed Jul. 2, 2009, entitled Mitotic Figure Detector And Counter System And Method For Detecting And Counting Mitotic Figures, which claims the benefit of U.S. Provisional Application No. 61/077,966, filed Jul. 3, 2008, and U.S. patent application Ser. No. 12/496,802 filed Jul. 2, 2009 entitled Epithelial Layer Detector And Related Methods, which claims the benefit of U.S. Provisional Application No. 61/077,974, filed Jul. 3, 2008. The entire disclosures of U.S. patent application Ser. No. 12/496,785 filed Jul. 2, 2009, entitled Mitotic Figure Detector And Counter System And Method For Detecting And Counting Mitotic Figures, and U.S. patent application Ser. No. 12/496,802 filed Jul. 2, 2009 entitled Epithelial Layer Detector And Related Methods, are incorporated herein by reference.

FIELD

The present disclosure relates to digital pathology. More particularly, the present disclosure relates to a signet ring cell detector and corresponding method for automatically detecting signet ring cells in of a tissue sample.

BACKGROUND OF THE INVENTION

Digital pathology involves the use of computers to assist pathologists in grading tissue specimens. For example, a tissue sample for breast carcinoma diagnosis typically takes an expert five minutes or more to grade. Several studies have demonstrated low agreement among pathologists' grading of the same case, questioning the objectivity of their diagnosis. A successful system may assist the pathologist in diagnosis, helping to achieve more reproducible results at lower cost.

The identification of signet ring cells is important for diagnosis of signet ring cell carcinoma, which is a particularly deadly form of gastric cancer, because there are no easily detectable markers besides the signet ring cells. Because the signet ring cells may occur in small number, they may be easily missed by human pathologists.

Accordingly, an apparatus/method is needed for automatically detecting signet ring cells in of a tissue sample.

SUMMARY OF INVENTION

A method is disclosed herein for automatically detecting signet ring cells in an image of a biopsy tissue sample. The method comprises: finding in the image, in a computer process, points about which cell membranes appear in radial symmetry; selecting as candidate points, in a computer process, at least ones of the points that have an adjacent nuclei with a predetermined shape feature; and applying a convolutional neural network computer process to the candidate points to determine which of the candidate points are signet ring cells.

Further disclosed herein is a signet ring cell detector for automatically detecting signet ring cells in an image of a biopsy tissue sample. The detector comprises: a radial symmetry finder for finding in the image points about which cell membranes appear in radial symmetry; a candidate selector for selecting as candidate points, at least ones of the points that have an adjacent nuclei with a predetermined shape feature; and a convolutional neural network unit for determining which of the candidate points are signet ring cells.

DETAILED DESCRIPTION

Figure 7:
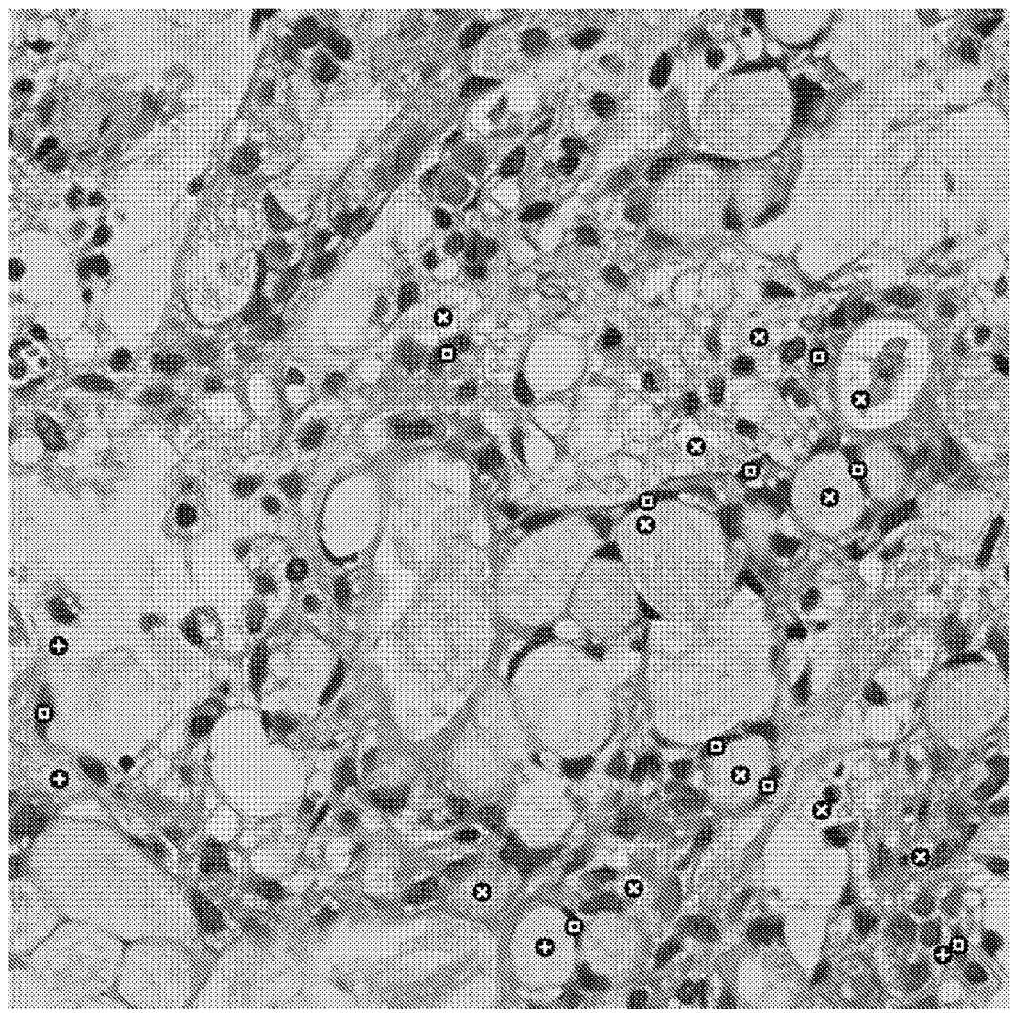
FIG. 7 is a digital high-resolution color scan or image of a biopsy tissue sample illustrating each step of the classification or detection of signet ring cells: squashed nucleous detection, the search for nearby Hough peaks, and the classification of those peaks.

FIG. 7 is a digital high-resolution color scan or image of a biopsy tissue sample which may or may not contain signet ring cells. Each squashed nucleus is marked with a square, each nearby negative Hough peak is marked with a plus (+), and each nearby positive Hough peak (center of a signet ring cell) is marked with a cross (X).

Figure 1:
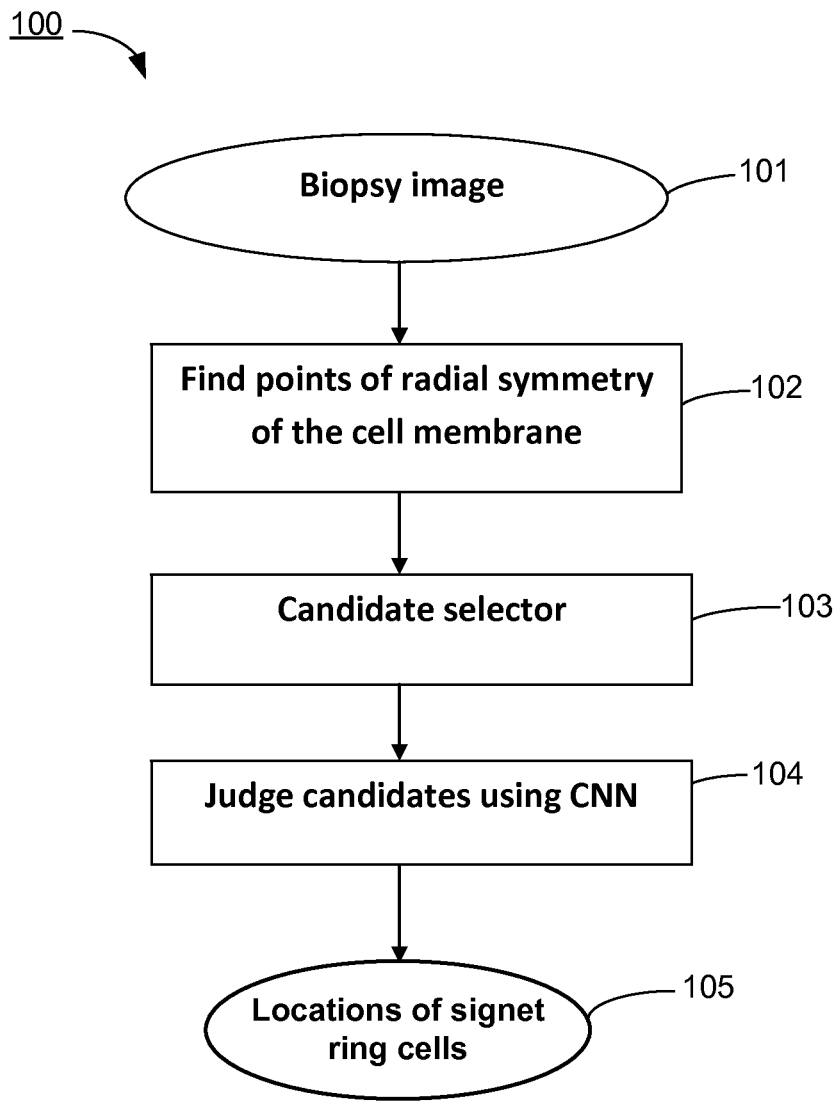
FIG. 1 is a block diagram of an exemplary embodiment of a signet ring cell (SRC) detector for automatically identifying signet ring cells in a tissue sample.

FIG. 1 is a block diagram of an exemplary embodiment of a signet ring cell (SRC) detector 100 for automatically identifying signet ring cells in a tissue sample. The SRC detector 100 includes a radial symmetry finder 102, a candidate selector 103, and a convolutional neural network (CNN) unit 104. The tissue sample may be prepared for analysis by the SRC detector 100 by staining it with two different colored dyes, such as but not limited to hematoxylin, which typically images with a dark cyan color, and eosin, which typically images with a light magenta color. Then, one or more digital high-resolution color scans or images (e.g. digital micrographs) 101 of the dyed stained tissue sample is/are obtained with a digital imaging device. The high-resolution color scan(s) or image(s) 101 of the tissue sample is/are applied to an input of the radial symmetry finder 102. The radial symmetry finder 102 looks for and generates a list of candidate signet ring cell centers by geometrically preprocessing the color scan(s) or image(s) by determining points around which the cell membrane appears radially symmetric. Because squashed nuclei are known to appear on peripheries of signet ring cells (FIG. 7), the candidate selector 103 identifies such squashed nuclei and eliminates some of candidate signet ring cells from the list by analyzing the points at the output of the radial symmetry finder 102 to identify those points, i.e., candidate points, which appear to have squashed nuclei, thus, only the candidate cell centers with squashed nuclei nearby remain as candidates on the list. In other words, the candidate selector 103 looks for the distinctive, squashed shape of the signet ring cell nucleus. It attempts to isolate the nucleus based on color and then feeds the nuclear-colored portion to the CNN unit 104. Color thresholds are pre-determined (not adjusted for each input). The CNN unit 104 analyzes each remaining candidate signet ring cell (a full color frame centered at the candidate point) to determine whether the candidate has an overall cell configuration that appears like a signet ring cell and identifies candidates that are signet ring cells 105.

Figure 2:
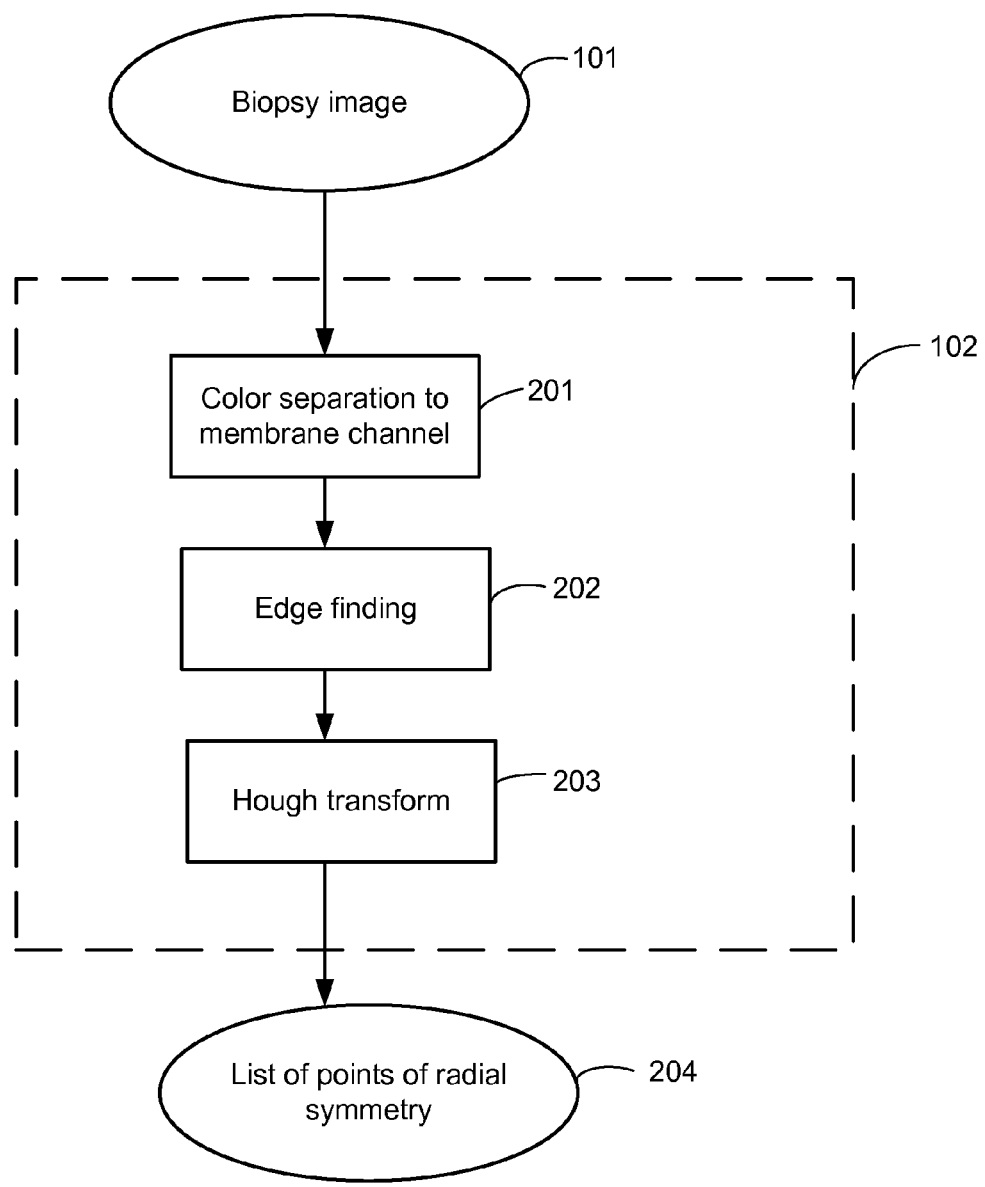
FIG. 2 is a block diagram of an exemplary embodiment of a radial symmetry finder.

FIG. 2 is a block diagram of an exemplary embodiment of the radial symmetry finder 102. The radial symmetry finder 102 includes a color separator 201, an edge finder 202, and a Hough transform unit 203. The color separator 201 isolates a color channel as the "membrane channel." The membrane color will depend on the dyes used. For example, cell membranes are eosiniphilic, and eosin images strongly in the green channel. In an exemplary embodiment designed for hematoxylin and eosin-stained tissues, the color separator 201 performs a simple separation into red, green, and blue color channels on each of the high-resolution scan(s) or image(s) 101 of the tissue sample, and designates the green channel as the membrane channel.

The edge finder 202 identifies edges in the membrane channel that are likely to represent cell membranes. Edge detection methods such as the Sobel algorithm provide information about the image intensity change in any given direction, and the results of these edge detectors may be collected in several directions. In an exemplary embodiment, the membrane channel is first enhanced with a nonlinear filter, and the edge finder 202 operates in horizontal, vertical, and diagonal directions to produce four edge maps of the enhanced membrane channel.

The Hough transform unit 203 computes a generalized Hough transform on the remaining region from the four edge maps and outputs a list of candidate points of radial symmetry 204 for signet ring cells. In general, the Hough transform of a greyscale bitmap B at (x,y) is $$H(x, y) = \frac{1}{C} \int_0^\pi \int_{r_1}^{r_2} f\left(\begin{array}{c} B(x + r\cos\theta, y + r\sin\theta), \\ B(x - r\cos\theta, y - r\sin\theta) \end{array}\right) dr\, d\theta$$

where f(a,b) is one if a and b both exceed a given threshold, and zero otherwise. Thus, H(x,y) measures the radial symmetry about (x,y). In the present disclosure, a discretized version of this transform is applied, using the four edge maps in each π/4 interval of the integral. The candidate points for signet ring cells are selected as the peaks of this transform achieving a given threshold, provided that no two peaks are selected too close together. These candidate points may be filtered to exclude those outside a certain candidate region. The candidate region excludes areas that match predetermined color criteria (white or blood-colored regions) and points that appear too close to an edge detected by the edge finder 202.

The radial symmetry finder 102 also includes an extractor (not shown) that frames around each of the candidate points of radial symmetry 204 and applies each of the framed candidate points 205 (FIG. 3) to the candidate selector 103.

Figure 3:
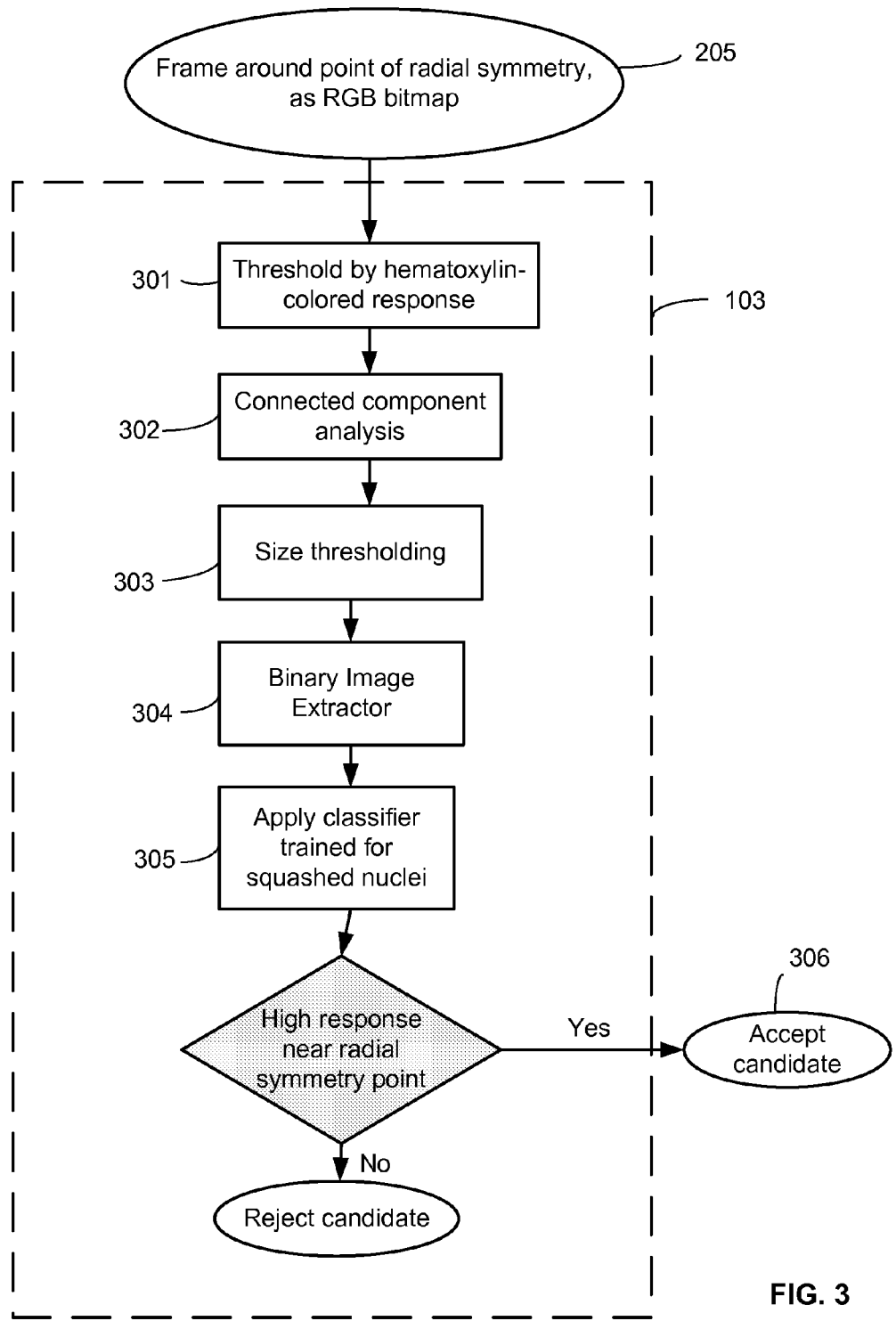
FIG. 3 is a block diagram of an exemplary embodiment of a candidate selector.

FIG. 3 is a block diagram of an exemplary embodiment of the candidate selector 103. The candidate selector 103 finds nuclei of a distinctive "squashed" shape that are known to appear on the periphery of signet ring cells. The candidate selector 103 includes a color threshold prediction unit 301, a connected component analyzer 302, a shape filtering unit 303, a binary image extractor 304, and a classifier unit 305. The thresholding unit 301 accepts or rejects individual pixels of the biopsy image 101, by comparing their color to the expected color of a nucleus. In an exemplary embodiment designed for tissues where the dyes include hematoxylin, this color will be hematoxylin-rich. The result of 301 is a binary image in which the pixel color (white or black) indicates whether or not the pixel in the color image 101 has the expected nucleus color.

The connected component analyzer 302 extracts groups of nuclear-colored pixels in the binary image output from the color threshold prediction unit 301 that are connected to one another. Those groups of connected pixels are referred to further-on as blobs.

The shape filtering unit 303 filters out blobs that do not meet certain basic shape constraints. At a minimum, shape constraints include size (width, height, mass) of blobs, but can also include more complex shape constraints that characterize the typical 'squashed nucleus' shape present in signet ring cells. An example of such complex shape constraint is the ratio of the long axis of the blob over its short axis. A binary image extractor 304 then extracts a binary image around the blob to be sent to the classifier unit 305.

Figure 5:
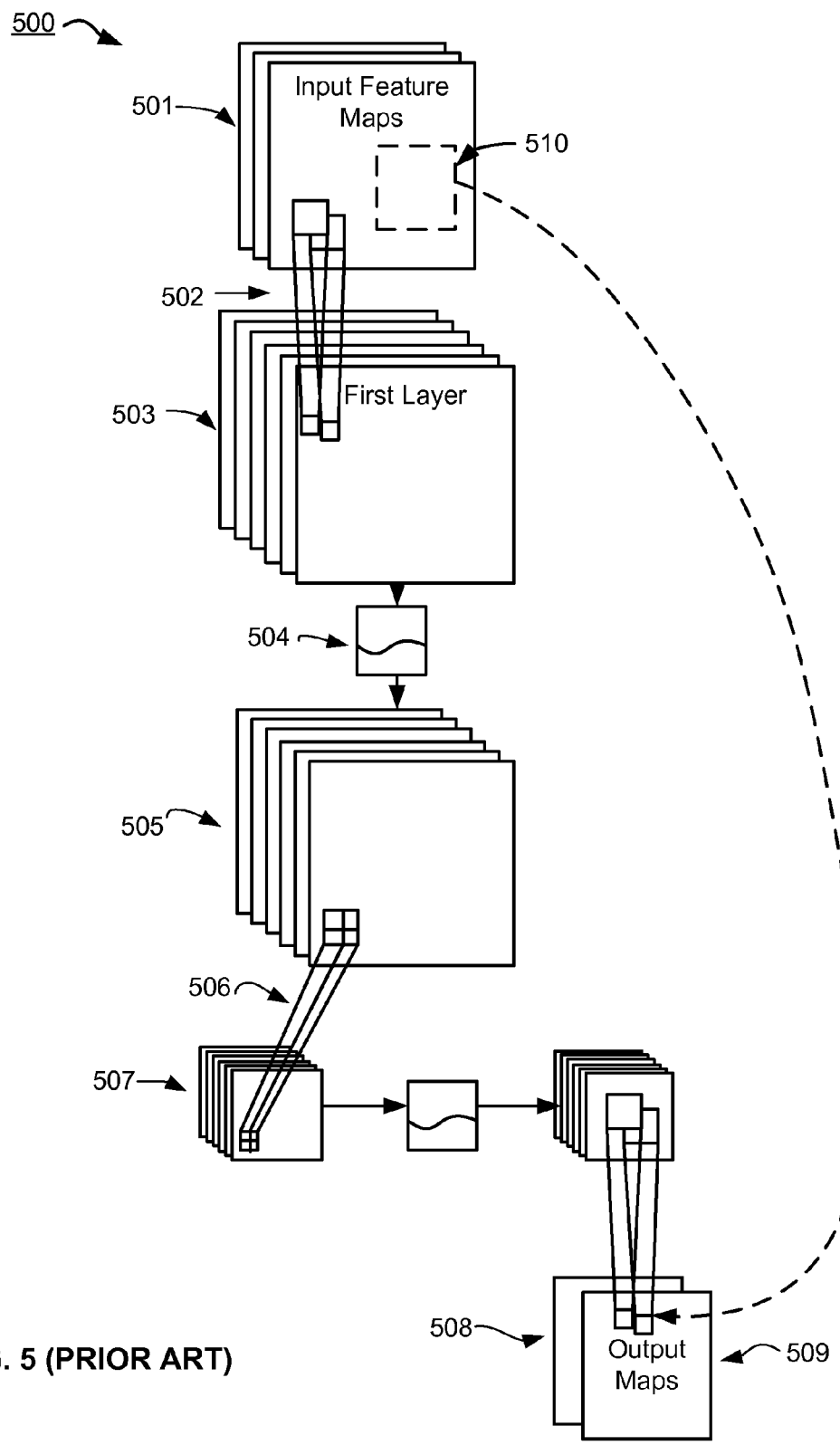
FIG. 5 schematically illustrates a conventional convolutional neural network (CNN).

The classifier unit 305 comprises a classifier trained as a squashed nucleus detector. In one exemplary embodiment, the classifier unit 305 comprises a CNN. FIG. 5 schematically depicts a conventional CNN 500. The structure and function of CNN 500 is well known in the art. The CNN convolves a stack of inputs 501 (input layer), referred to as feature maps, with small filters 502 to obtain a new stack of feature maps, referred to as an internal layer or first internal layer 503. Each of the feature maps in this first internal layer 503 is obtained by convolving one or more of the input maps with trained kernels (usually having different weights), and adding together the results. The resulting values are then passed through a non-linear transfer function 504 to obtain second internal layer 505. A third internal layer 507 is obtained by subsampling 506, wherein each value is obtained by averaging together a group of adjacent values from the previous internal layer (e.g., second internal layer 505). The groups do not overlap, so the resulting internal layer is substantially smaller than the previous internal layer. After several internal layers, it is clear that each value 509 in output layer 508 depends on an input window 510 of adjacent values in the input layer 501. Furthermore, these windows overlap with one another.

In another exemplary embodiments, the classifier unit 305 comprises, without limitation, a support vector machine (SVM).

Referring again to FIG. 3, the classifier unit 304, trained for squashed nuclei, further prunes the candidate points for signet ring cells by checking whether a squashed-shaped nucleus is present on the periphery. The input to the classifier unit 304, in one exemplary embodiment, comprises one feature map, which is a 48×48 binary image at magnification of 4.3895 dots per micron. This feature map is centered at the center of a pixel group obtained from shape filtering unit 303. The classifier unit 304 outputs a classification for each pixel group from shape filtering unit 303. Such a classifier unit may be trained on a supply of pixel groups from the shape filtering unit 303 that appear on the periphery of known signet ring cells, against pixel groups from the shape filtering unit 303 that are not known appear on the periphery of a signet ring cell. When a positive classification is obtained (indicating a shape resembling the nuclei found around signet ring cells the classifier unit 305 was trained for), and it is within a prescribed distance of the point of radial symmetry 204 (FIG. 2), the point of radial symmetry 204 is accepted as a candidate 306 point.

Figure 4:
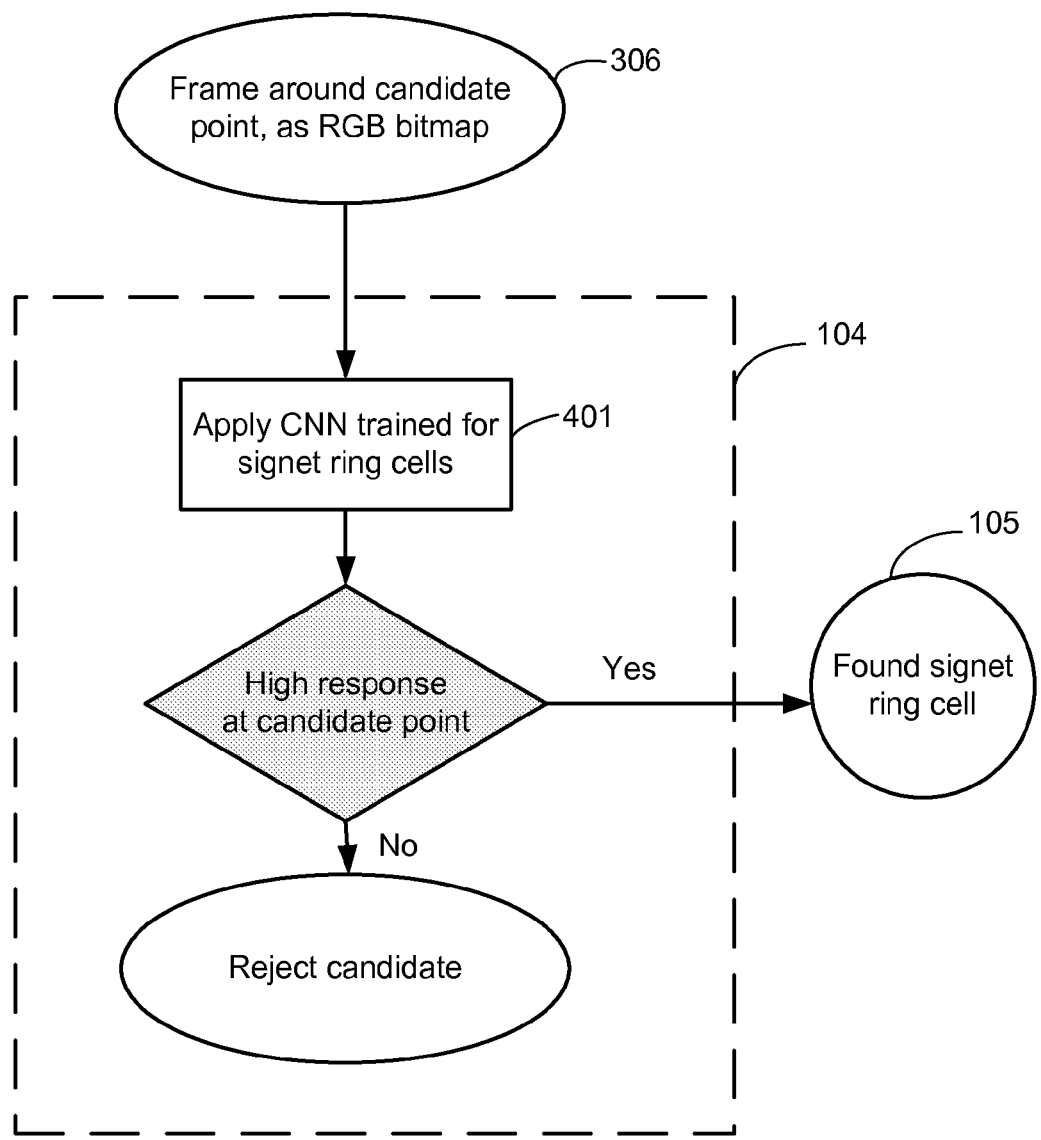
FIG. 4 is a block diagram of an exemplary embodiment of a CNN for judging candidate signet ring cell points to identify or detect signet ring cells.

Referring to FIG. 4, the CNN unit 104 comprises a CNN 401 trained for judging the candidate SRC points to identify or detect signet ring cells. When a Hough peak occurs near a squashed nucleus (a candidate point at the output of the classifier unit 305 of the candidate selector 103), the CNN 401 judges the overall configuration of the tissue around the candidate point, to make a final judgment as to whether or not a signet ring cell is present. In one exemplary embodiment, the CNN 401 utilizes red, green, and blue color channels, in a 204×204 (at 40×) frame about the Hough peak. As the CNN 401 incorporates color information and judges more than shape, it requires more capacity than the classifier unit 305 for squashed nuclei. More specifically, to perform this classification, the CNN 401 may be trained on a supply of candidate points known to be signet ring cells, against a supply of candidate points 306 output from the classifier unit 305 that are not signet ring cells.

One skilled in the art will recognize that the signet ring cell detector and methods described herein, may be implemented using any suitably adapted computer system. The computer system may include, without limitation, a mainframe computer system, a workstation, a personal computer system, a personal digital assistant (PDA), or other device or apparatus having at least one processor that executes instructions from a memory medium.

The computer system may include one or more memory mediums on which one or more computer programs or software components may be stored. The one or more software programs which are executable to perform the methods described herein, may be stored in the memory medium. The one or more memory mediums may include, without limitation, CD-ROMs, floppy disks, tape devices, random access memories such as but not limited to DRAM, SRAM, EDO RAM, and Rambus RAM, non-volatile memories such as, but not limited hard drives and optical storage devices, and combinations thereof. In addition, the memory medium may be entirely or partially located in one or more associated computers or computer systems which connect to the computer system over a network, such as the Internet.

The signet ring cell detector and methods described herein may also be executed in hardware, a combination of software and hardware, or in other suitable executable implementations. The methods implemented in software may be executed by the processor of the computer system or the processor or processors of the one or more associated computers or computer systems connected to the computer system.

Figure 6:
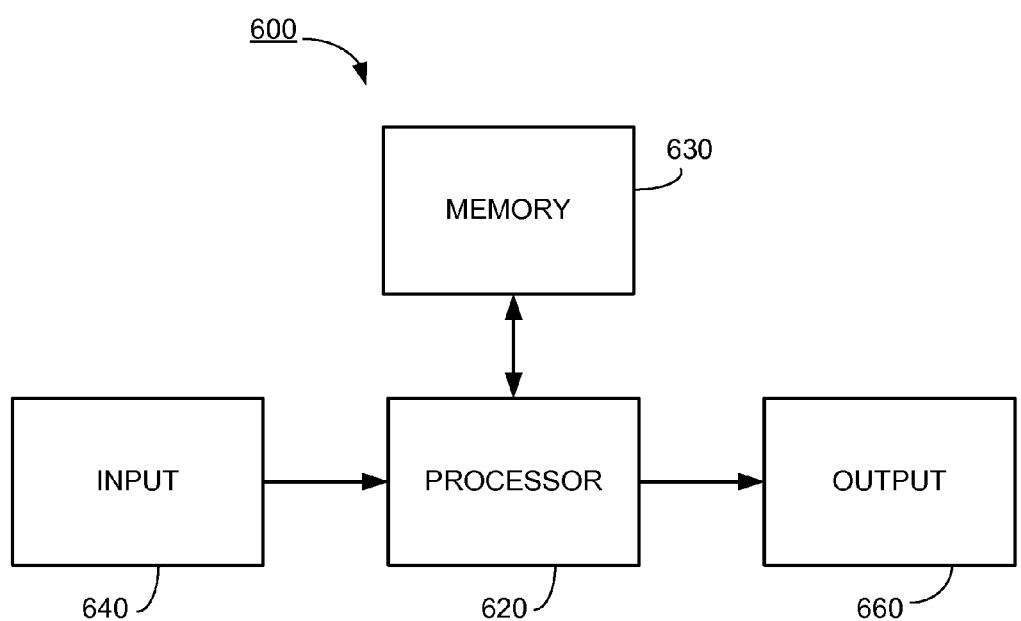
FIG. 6 is a block diagram of an exemplary embodiment of a computer system for implementing the SRC detector and methods described herein.

FIG. 6 is a block diagram of an exemplary embodiment of a computer system 600 for implementing the signet ring cell detector and methods described herein. The computer system 600 includes a processor 620, a memory 630 for storing one or more programs which are executable by the processor 620 for implementing the signet ring cell detector and methods described herein, an input 640 for receiving input data, e.g., unlabeled color scan data and labeled color scan data (training data), and an output 660 for outputting data, e.g., one or more predicted labels indicating the candidate point(s) that are signet ring cells and one or more predicted labels indicating the candidate point(s) that are not signet ring cells.

While exemplary drawings and specific embodiments of the present disclosure have been described and illustrated, it is to be understood that that the scope of the invention is not to be limited to the particular embodiments discussed. Thus, the embodiments shall be regarded as illustrative rather than restrictive, and it should be understood that variations may be made in those embodiments by workers skilled in the arts without departing from the scope of the invention as set forth in the claims that follow and their structural and functional equivalents.

What is claimed is:

1. A method for automatically detecting signet ring cells in an image of a biopsy tissue sample, the image comprising at least two different colors, one of the at least two different colors most likely representing cell membranes, the method comprising the steps of:

in a computer process, separating a portion of the image comprising the one of the at least two different colors that most likely represents the cell membranes from a portion of the image comprising the other one of the at least two different colors;

in a computer process, identifying edges in the portion of the image comprising the one of the at least two different colors that most likely represent the cell membranes using image intensity change in a plurality of directions, wherein the identified edges are likely the cell membranes;

from the identified edges likely to be cell membranes, determining, in a computer process, points around which the cell membranes appear radially symmetric, each of the points representing the center of a possible signet ring cell;

selecting as candidate signet ring cells, in a computer process, ones of the points representing the centers of possible signet ring cells that have an adjacent nucleus with a squashed shape by, for each of the points representing the center of a possible signet ring cell:

comparing the color of each pixel of the image to an expected color of a nucleus and classifying pixels having the expected color of the nucleus as nuclear pixels;

extracting any connected group of the nuclear pixels from the image;

determining whether the extracted connected group of nuclear pixels has a nucleus with the squashed shape on a periphery thereof; and selecting that point as a center of a candidate signet ring cell; and applying a convolutional neural network computer process to the selected points representing the centers of the candidate signet ring cells to determine which of the candidate signet ring cells are signet ring cells.

2. The method of claim 1, wherein the step of determining points around which the cell membranes appear radially symmetric includes the step of finding peaks of a Hough transform wherein the points representing the centers of possible signet ring cells are selected as the peaks of the transform achieving a given threshold.

3. The method of claim 1, wherein the selecting step is performed with a classifier.

4. The method of claim 3, wherein the classifier comprises a convolutional neural network computer process.

5. The method of claim 3, wherein the classifier comprises a support vector machine computer process.

6. The method of claim 1, wherein the step of applying the convolutional neural network computer process is performed with a convolutional neural network computer trained on a supply of candidate points known to be signet ring cells, against a supply of candidate points that are not signet ring cells.

7. A signet ring cell detector for automatically detecting signet ring cells in an image of a biopsy tissue sample, the image comprising at least two different colors, one of the at least two different colors most likely representing cell membranes, the detector comprising:

a processor executing instructions for:

separating a portion of the image comprising the one of the at least two different colors that most likely represents the cell membranes from a portion of the image comprising the other one of the at least two different colors;

identifying edges in the portion of the image comprising the one of the at least two different colors that most likely represent the cell membranes using image intensity change in a plurality of directions, wherein the identified edges are likely the cell membranes;

from the identified edges likely to be cell membranes, determining points around which the cell membranes appear radially symmetric, each of the points representing the center of a possible signet ring cell;

selecting as candidate signet ring cells, ones of the points representing centers of possible signet ring cells that have an adjacent nucleus with a squashed shape by, for each of the points representing the center of a possible signet ring cell:

comparing the color of each pixels of the image to an expected color of a nucleus and classifying pixels having the expected color of the nucleus as nuclear pixels;

extracting any connected group of the nuclear pixels from the image;

determining whether the extracted connected group of nuclear pixels has a nucleus with the squashed shape on a periphery thereof; and selecting that point as a center of a candidate signet ring cell; and applying a convolutional neural network to the selected points representing the centers of the candidate signet ring cells to determine which of the candidate signet ring cells are signet ring cells.

8. The detector of claim 7, wherein instructions for determining points around which the cell membranes appear radially symmetric include instructions for:

finding peaks of a Hough transform wherein the points representing the centers of possible signet ring cells are selected as the peaks of the transform achieving a given threshold.

9. The detector of claim 7, wherein the selecting of that point as the center of the candidate signet ring cell is performed with a classifier.

10. The detector of claim 9, wherein the classifier comprises a convolutional neural network.

11. The detector of claim 9, wherein the classifier comprises a support vector machine.

12. The detector of claim 7, wherein the convolutional neural network comprises a convolutional neural network trained on a supply of candidate points known to be signet ring cells, against a supply of candidate points that are not signet ring cells.

* * * * *